(12) United States Patent
Geissler et al.

(10) Patent No.: US 11,478,459 B2
(45) Date of Patent: Oct. 25, 2022

(54) PHARMACEUTICAL PREPARATION

(71) Applicant: Merck Patent GmbH, Darmstadt (DE)

(72) Inventors: Simon Geissler, Bad Homburg (DE); Stefan Schiller, Darmstadt (DE); Meike Harms, Darmstadt (DE); Holger Kubas, Bad Homburg (DE); Markus Weigandt, Mannheim (DE); Michael Lange, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/637,822

(22) PCT Filed: Aug. 8, 2018

(86) PCT No.: PCT/EP2018/071545
§ 371 (c)(1),
(2) Date: Feb. 10, 2020

(87) PCT Pub. No.: WO2019/030302
PCT Pub. Date: Feb. 14, 2019

(65) Prior Publication Data
US 2020/0237733 A1    Jul. 30, 2020

(30) Foreign Application Priority Data

Aug. 11, 2017   (EP) .................... 17186010.9

(51) Int. Cl.
| | |
|---|---|
| *A61K 31/437* | (2006.01) |
| *A61K 9/00* | (2006.01) |
| *A61K 9/16* | (2006.01) |
| *A61K 9/20* | (2006.01) |
| *A61K 9/28* | (2006.01) |
| *A61K 9/48* | (2006.01) |
| *A61K 47/38* | (2006.01) |

(52) U.S. Cl.
CPC .......... *A61K 31/437* (2013.01); *A61K 9/0053* (2013.01); *A61K 9/16* (2013.01); *A61K 9/1694* (2013.01); *A61K 9/2077* (2013.01); *A61K 9/2095* (2013.01); *A61K 9/2893* (2013.01); *A61K 9/4833* (2013.01); *A61K 9/4866* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 9,000,153 B2 * | 4/2015 | Fuchss | A61P 35/04 544/126 |
| 9,598,408 B2 | 3/2017 | Fuchss et al. | |
| 2016/0038496 A1 * | 2/2016 | Shu | A61P 35/00 514/262.1 |

FOREIGN PATENT DOCUMENTS

WO      12028233 A1    3/2012

OTHER PUBLICATIONS

Tu Van Duong et al, "The role of the carrier in the formulation of pharmaceutical solid dispersions. Part II: amorphous carriers", Expert Opinion on Drug Delivery, Jun. 17, 2016 (Jun. 17, 2016), p. 1-14.
Abhishek Singh et al, "Spray drying formulation of amorphous solid dispersions", Advanced Drug Delivery Reviews, vol. 100, May 1, 2016 (May 1, 2016), p. 27-50.
International Search Report PCT/EP2018/071545 dated Oct. 19, 2018 (pp. 1-3).

* cited by examiner

*Primary Examiner* — Nannette Holloman
(74) *Attorney, Agent, or Firm* — Millen White Zelano & Branigan, PC; Brion P. Heaney

(57) ABSTRACT

The present invention relates to a solid pharmaceutical preparation of 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile, a method of making same, and medical uses thereof.

25 Claims, 4 Drawing Sheets

PHARMACEUTICAL PREPARATION

The present invention relates to a solid pharmaceutical preparation of 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile, as well as a method of making same, as well as medical uses thereof.

3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile is disclosed as Example 36 in WO 2012/028233 A1, as one member of a family of imidazo[4,5 c]quinolines, which have been found to have valuable pharmacological properties. It is a highly potent (1050<1 nM) and selective inhibitor of Ataxia telangiectasia mutated (ATM) kinase, a signaling kinase crucial for DNA double strand break repair and checkpoint control. The small molecule inhibitor thereby synergistically potentiates the effect of DNA damaging agents such as radiotherapy and DSB inducing cytotoxic agents such as Topotecan® (Novartis). It can therefore be used, in particular, for the sensitization of cancer cells to anticancer agents and/or ionizing radiation.

3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile has a very low solubility in water and biorelevant media. In detail 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile has a solubility in Fasted Simulated Intestinal Fluid (FaSSIF) of 0.25 µg/mL and in FedState Simulated Intestinal Fluid (FeSSIF) of 1 µg/mL. Despite such low solubility rather high doses of above 100 mg are needed for its use in the therapy. With an estimated efficacious human dose of >100 mg, the compound has a dose/solubility ratio of at least 100,000 and can be classified as DCS IIb (Butler and Dressman, 2010) so that a pharmaceutical preparation providing the bioavailability that is necessary for its therapeutic is difficult to achieve. Additionally, the size of the resulting dosage form needs to be suitable for oral administration.

3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile strongly tends to recrystallize and also melts under degradation. Thus, preparation of a non-stabilized pure amorphous compound is difficult. Additionally, the amorphous state for this compound is rather unstable due to the very high recrystallization tendency.

It was therefore an object of the present invention to provide a pharmaceutical dosage form of 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile that would provide sufficient bioavailability, and a suitable process for its manufacture.

Various attempts to provide a suitable pharmaceutical preparation that provides a bioavailability of 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile in an amount necessary for its use in therapy such as oral solutions, self-micro-emulsifying drug delivery system SMEDDS failed. For example, an oral solution that can be administered to the patient to provide the API in an amount sufficient for therapy was not obtainable without addition of a high concentration of sodium dodecyl sulfate (SDS) that is not acceptable from the toxicological point of view. Further, SMEDDS or emulsions cannot be prepared due to the low solubility of the compound in the tested oils.

SUMMARY OF THE INVENTION

The present invention is directed to a composite comprising a solid dispersion of 3-Fluoro-4-[7-methoxy-3-methyl-8-(1-methyl-1H-pyrazol-4-yl)-2-oxo-2,3-dihydro-imidazo[4,5-c]quinolin-1-yl]benzonitrile, or a pharmaceutically acceptable salt thereof, in a polymeric matrix.

3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile is illustrated below:

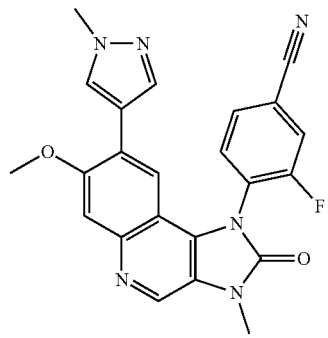 [SMILES: COc1cc2ncc3c(c2cc1-c1cnn(C)c1)n(-c1ccc(C#N)cc1F)c(=O)n3C]

3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile, in any form, is hereinafter also referred to as "Compound".

The present invention further pertains to a pharmaceutical preparation comprising said composite, methods of preparing the composite and methods of preparing the pharmaceutical preparation, as well as the use of the composite respectively pharmaceutical preparation in the treatment of cancer, either alone or in combination with radiotherapy and/or chemotherapy.

The term "composite" as used herein means a three-dimensional solid pharmaceutical preparation comprising an active pharmaceutical ingredient (API) and at least one pharmaceutically acceptable excipient. This "composite" may be processed to other pharmaceutical preparations such as, for example tablets, but may also be administered to the patient directly without any modification.

The term "polymeric matrix", as used herein, describes a three-dimensional solid that is formed by one or more than one polymer. In the composite of the present invention the polymeric matrix is used to embed the Compound. Further compounds such as, for example, one or more further APIs or other excipients, can be incorporated, such as dissolved or dispersed, in such polymeric matrix.

In one aspect, the present invention provides a composite comprising a solid dispersion of the Compound, or a pharmaceutically acceptable salt thereof, in a polymeric matrix. In some embodiments, the composite may comprise the solid dispersion as well as one or more pharmaceutically acceptable excipients, for instance selected from a filler (e.g. polysaccharide, disaccharide, polyalcohols), disintegrant (e.g. polyvinylpolypyrrolidone, modified polysaccharides), non-ionic and ionic surfactants (e.g. poloxamer, sodium lauryl sulphate), plasticizers (e.g. polyalkylene glycol, triacetin, citrate esters and phthalate esters) and inorganic absorbers (e.g. silica).

The term "solid dispersion", as used herein, refers to a drug substance, which is dispersed or distributed in a dispersion medium, which is a polymeric matrix in accordance with the present invention. Based upon the possible combinations of the drug substance and polymer physical states, the drug substance can be either crystalline or amorphous and the polymeric matrix can also be crystalline and amorphous, resulting in four possible combinations: crystalline drug substance crystalline polymer (solid suspension); amorphous drug substance amorphous polymer; crystalline drug amorphous polymer; and amorphous drug—crystalline polymer.

Preferred embodiments herein relate to amorphous drug substance in polymeric matrix. Amorphous drug substance can be dispersed in the form of amorphous (micro)particles in an amorphous polymeric matrix, which is then referred to as an amorphous suspension, or it can be molecularly dispersed in a polymer or polymeric matrix to form a solid solution. According to a preferred embodiment of the present invention, both, the Compound and the polymer are present in amorphous state.

The term "solid solution" as used herein, shall still encompass those embodiments wherein a small portion of the drug substance may have come out of solution or remain undissolved, provided that at least about 80%, more preferably at least about 90% and most preferably at least about 95% or at least about 99% of the drug substance (by volume) shall be in the molecularly dispersed state. In such a solid solution, the individual physical properties of the drug substance are no longer recognizable.

The term "about" as used herein refers to a numeric value, including, for example, whole numbers, fractions, and percentages, whether or not explicitly indicated. The term "about" generally refers to a range of numerical values (e.g., +/−1-3% of the recited value) that one of ordinary skill in the art would consider equivalent to the recited value (e.g., having the same function or result). In some instances, the term "about" may include numerical values that are rounded to the nearest significant figure.

In a preferred embodiment, the composite according to the present invention consists of the solid dispersion of 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile, or a pharmaceutically acceptable salt thereof, in the polymeric matrix. Of course, it may then simply be referred to as the solid dispersion.

Most preferably, the solid dispersion is a solid solution. Accordingly, the present invention is also directed to the composite, wherein the solid dispersion is a solid solution.

While 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile may be present in any suitable salt form, it is most preferably present in its free form, rather than a salt form.

Pharmaceutically acceptable salts include those mentioned in the disclosure of WO 2012/028233 A1, which is incorporated by reference herein in its entirety. Such salts include, for example, oxalate or maleate salts.

Any reference to amounts or weights or weight percentages of 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile or pharmaceutically acceptable salts thereof, shall be taken to refer to the anhydrous free form of 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile, unless specified otherwise herein.

In order to form a solid dispersion, the polymer or polymers forming the polymeric matrix are generally polymers that are capable of embedding the drug substance, especially in a melt granulation or melt extrusion process or when dissolved in a solvent and atomized, especially in a spray-drying process. Alternatively, the solid dispersion may be also prepared by a co-precipitation process.

Any polymer capable of embedding the drug substance, most preferably at a molecular level, and enhancing its dissolution may be used in the context of the present invention. Hydrophilic polymers are therefore preferred. Especially preferred are polymers that contain an ionic group such as a carboxyl group, and that are insoluble below and soluble above a certain pH value in the range of from about pH 5 to about pH 6.2 or amphiphilic polymers. Accordingly, a preferred embodiment of the invention is directed to a polymeric matrix that comprises or consists of a polymer that contains an ionic group such as a carboxyl group, and that are insoluble below and soluble above a certain pH value in the range of from about pH 5 to about pH 6.2 or to a polymeric matrix that comprises or consists of an amphiphilic polymer.

The term "amphiphilic polymer", as used herein means that the polymeric material has distinct hydrophilic and hydrophobic portions. "Hydrophilic" typically means a portion that interacts intramolecularly with water and other polar molecules. "Hydrophobic" typically means a portion that interacts preferentially with oils, fats or other non-polar molecules rather than aqueous media Examples of polymers that are insoluble below and soluble above a certain pH value in the range of from pH 5 to pH 6.2 and that are suitable for forming the polymeric matrix of the composite are hydroxypropyl methylcellulose phthalate (HPMCP), hydroxypropyl methylcellulose acetate succinate (HPMCAS), cellulose acetate phthalate (CAP), polyvinyl acetate phthalate (PVAP), cellulose acetate trimellitate (CAT), hydroxypropyl methylcellulose acetate trimellitate (HPMCAT), poly(methacrylic acid-co-ethyl acrylate) (Eudragit® L100-55) and poly(methacrylic acid-co-methyl methacrylate) (Eudragit® L and Eudragit® S), whereby HPMCP, HPMCAS, CAP, PVAP, CAT and HPMCAT are preferred. An example for a preferred amphiphilic polymer is a polyvinyl caprolactampolyvinyl acetate polyethylene glycol graft copolymer (PVAc-PVCap-PEG), (Soluplus®). Accordingly, the present invention is also directed to a composite, wherein the polymer is hydroxypropyl methylcellulose phthalate (HPMCP), hydroxypropyl methylcellulose acetate succinate (HPMCAS), cellulose acetate phthalate (CAP), polyvinyl acetate phthalate (PVAP), cellulose acetate trimellitate (CAT) or hydroxypropyl methylcellulose acetate trimellitate (HPMCAT) or a polyvinyl caprolactampolyvinyl acetate polyethylene glycol graft copolymer (PVAc-PVCap-PEG).

Especially preferred is cellulose acetate phthalate. Accordingly, an especially preferred embodiment of the invention is directed to the composite, wherein the polymeric matrix comprises or consists of cellulose acetate phthalate. Cellulose acetate phthalate is also named as Cellacefate NF or Cellulose Acetate Phthalate, is specified in various pharmacopoeia such as USP/NF, EP, JP, and can be obtained, for example from Eastman Chemical Company.

The polymeric matrix in the solid dispersion according to the present invention may comprise more than one polymer forming the matrix. In preferred embodiments, however, the polymeric matrix comprises only one polymer. In addition, the polymeric matrix may comprise one or more additional pharmaceutical excipient, such as plasticisers, solubilizers, pH modifiers, antioxidants and osmogens.

Exemplary plasticizers known in the art include polyalkylene glycol, tributyl citrate, triethyl citrate, acetyltriethyl citrate, acetyltributyl citrate, citric acid monohydrate, triacetin, dioctyl phthalate, diethyl phthalate, dibutyl sebacate, castor oil and derivatives thereof, e.g. PEG-40 hydrogenated castor oil.

Exemplary solubilizers include e.g. polyoxyethylene-polyoxypropylene block copolymer (e.g. Kolliphor® P188, P338, P407), polysorbate (e.g. Tween®), sodium dodecyl sulfate (SDS). Exemplary pH modifiers include phosphates, citrates, acetates, maleates, tartrates, succinates, lactates, carbonates, tris(hydroxymethyl)aminomethane, arginine, glycine, glycylglycine, histidine and lysine.

Exemplary antioxidants include ascorbic acid and its salts and derivates, butylated hydroxytoluene, vitamin E, tocopheryl polyethylene glycol succinate, butylated hydroxyanisol, sodium thiosulfate, sodium metabisulfite, methionine and lipoic acid.

Exemplary osmogens include salts such as mentioned under pH modifiers and further salts of sodium, potassium, magnesium, calcium or zinc and chloride, bromide, as well as sugars (e.g. glucose, sucrose, fructose, lactose, mannitol, sorbitol, trehalose, xylitol, inositol) and urea.

In some exemplary embodiments, additional pharmaceutically acceptable excipients are already provided in admixture with the polymer for forming the polymeric matrix. However, "polymer" as used herein is not to be understood as a blend of a polymer with additives, it shall refer to a polymer as such.

In preferred embodiments, the solid dispersion, more preferably solid solution, consists only of the drug substance in the polymeric matrix, which is formed by one polymer without any further additives (2-component-system).

The solid dispersion according to the present invention is obtainable, for instance, by melting processes e.g. hot melt extrusion or melt granulation, or by solvent-based processes, e.g. spray-drying, co-precipitation lyophilisation or solvent casting. Solvent-based approaches like co-precipitation, spray-drying, lyophilisation and solvent evaporation are preferred as it has been found to provide the most beneficial properties of the dispersion, respectively composite. Particularly preferred is spray-drying.

In suitable embodiments of the composite according to the invention, especially in the solid dispersion itself, the concentration of the Compound in the polymeric matrix is in range of from 4 to 50 percent (w/w), preferably from 10 to 30 percent (w/w), more preferably from 15 to 25 percent (w/w) and most preferably at about 20 percent (w/w) based upon the total weight of the composite. Accordingly, the present invention is also directed to the composite, wherein 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile is present in the polymeric matrix in a range of from 4 to 50 percent (w/w), preferably from 10 to 30 percent (w/w), more preferably from 15 to 25 percent (w/w) and most preferably at about 20 percent (w/w) based upon the total weight of the composite.

In an especially preferred embodiment, the solid dispersion consists of about 20% (w/w) 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile and about 80% (w/w) polymeric matrix, preferably made up by only one polymer without any further additives.

Depending from the process of its production the composite prepared by that may not be suitable to be directly used by the patient and needs further downstream processing to enable transfer into a pharmaceutical preparation such as a capsule or a tablet. For example, melt extrusion results in strands, that need to be cut or milled into smaller units and spray-drying may result in too fine small particles that need further granulation or compaction steps prior the preparation of tablets or filling into capsules.

If produced by spray-drying the particle size of the composite obtained is usually in a range that is character zed by a $d_{50}$ value from 1 μm to 300 μm, preferably from 20 μm to 200 μm and more preferably from 30 to 100 μm. Accordingly, one embodiment of the invention is also directed to the composite, wherein the composite has a mean particle size that is characterized by a $d_{50}$ value in the range from 1 μm to 300 μm, preferably from 20 μm to 200 μm and more preferably from 30 to 100 μm.

If the particle size is too small, it may be increased using suitable techniques such as granulation or roller compaction. Such techniques are used to prepare granulates that may have a particle size characterized by a $d_{50}$ value of 1000 μm or less, preferably 500 μm or less, more preferably 400 μm or less, 300 μm or less, for instance between 200 μm and 300 μm. Accordingly, the present invention is also directed to a granulate comprising the composite, wherein such granulate has a particle size that is characterized by a $d_{50}$ value of 1000 μm or less, preferably 500 μm or less, more preferably 400 μm or less, 300 μm or less, for instance between 200 μm and 300 μm.

Generally, a smaller particle size is associated with a higher surface area, which may be beneficial in terms of dissolution, but typically requires a mechanical decrease of the original particles, which is often associated with the generation of heat and may therefore have a negative impact on other physical parameters of the particles, such as density, but also the dispersion of drug substance within the matrix, the crystallinity of the compound and even impurity levels. The $d_{50}$ values referred to herein are measured by laser diffraction on a Malvern Mastersizer 2000 (dry method; micro volume tray; sample amount of 200 mg; dispersive air pressure of 0.1 bar; feed rate of 50%; measuring time of 4 s; obscuration of 1-5%; use of 66 dispersive steel balls a 2 mm; measurements evaluated with the MIE theory). The $d_{50}$ value referred to herein is the size in micrometres that splits the distribution with half above and half below this diameter. The $d_{50}$ is the median for a volume distribution and is often also designated Dv50 (or Dv0.5).

The term "spray-drying" as used herein refers, in principle, to a solvent extraction process. The constituents of the product to be obtained are dissolved/dispersed in a liquid and then fed, for example by using a peristaltic pump, to an atomiser of a spray-dryer. A suitable atomizer, which can be used for atomization of the liquid, include nozzles or rotary discs. With nozzles, atomization occurs due to the action of the compressed gas or pressurized liquid, while in case of using rotary discs atomization occurs due to the rapid rotation of the disc. In both cases, atomization leads to disruption of the liquid into small droplets into the drying chamber, wherein the solvent is extracted from the aerosol droplets and is discharged out, for example through an exhaust tube to a solvent trap.

The term "co-precipitation" as used herein generally refers to a process of precipitating two or more solid components (e.g., a polymeric carrier and an API) together from a common solution. Suitable solvents are capable to solve sufficient amounts of polymer and API and are mixtures of an aqueous solvent and an organic solvent, an organic solvent or a mixture of more than one organic solvent. Aqueous solvents include water and buffered solutions. Due to the low water solubility of the Compound the aqueous solvent present in a mixture of an aqueous solvent and an organic solvent is rather low, preferably in an amount ranging from about 0 to about 20% by volume. Suitable organic solvents that can be employed include but are not limited to alcohols such as, for example, ethanol, methanol, propanol, isopropanol and butanols. Other organic solvents include but are not limited to perfluorocarbons, acetone, dichloromethane, chloroform, ethyl acetate, methyl tert-butyl ether, acetonitrile, dimethyl formamide, dimethyl sulfoxide, dimethyl acetamide (N,N), N-Methyl-2-pyrrolidon and others. Preferable solvents for co-precipitation are dimethyl formamide, dimethyl sulfoxide, dimethyl acetamide (N,N), N-Methyl-2-pyrrolidon and mixtures thereof. More preferable is dimethyl sulfoxide. Precipitation of the components can be simultaneous or within close proximity thereto is promoted by diluting the solution into an antisolvent, temperature change, pH change, solvent removal, or the like. Suitable antisolvents have to show a very low solubility for both the API as well as the polymer. Possible antisolvents are aqueous solutions, organic solvents and mixtures thereof. Preferable antisolvents are acidic aqueous solutions, such as, for example, aqueous solutions containing citric acid, acetic acid, phosphoric acid, hydrochloric acid. More preferable is citric acid. The used solvent needs to be miscible with the antisolvent under the process conditions. All mentioned preferred solvents and antisolvents are fully miscible in all ratios. The Co-precipitation leads to formation of particles consisting of a polymeric matrix in which the API is embedded and is well known to those skilled in the art.

The term "lyophilisation" as used herein refers to a process of freeze-drying, which is a solvent removing process that includes freezing the material and then reducing the surrounding pressure to allow the frozen solvent in the material to sublimate directly from the solid phase to the gas phase. Although mainly used for dehydration, i.e. for removing of water, it can be also used for the removal of an organic solvent, a mixture of organic solvents or a mixture with an aqueous solvent with one or more organic solvents as they may be used for the preparation of the composite of the present invention. Lyophilisation of a solution of a polymer and an API leads to formation of a matrix, wherein the API is embedded in a polymer matrix formed.

The term "solvent-evaporation" as used herein refers to a process of solvent evaporation, which is a solvent removing process that due to reducing the surrounding pressure and/or increasing the temperature to allow the solvent in the material to evaporate directly from the liquid phase to the gas phase. It can be used for the removal of an organic solvent, a mixture of organic solvents or a mixture with an aqueous solvent with one or more organic solvents as they may be used for the preparation of the composite of the present invention. Solvent evaporation of a solution of a polymer and an API leads to formation of a matrix, wherein the API is embedded in a polymer matrix formed.

In principle, the solvent for spray-drying or solvent evaporation can be a mixture of an aqueous solvent and an organic solvent, an organic solvent or a mixture of more than one organic solvent. Aqueous solvents include water and buffered solutions. Due to the low water solubility of the Compound the aqueous solvent present in a mixture of an aqueous solvent and an organic solvent is rather low, preferably in an amount ranging from about 0 to about 20% by volume. Suitable organic solvents that can be employed include but are not limited to alcohols such as, for example, ethanol, methanol, propanol, isopropanol and butanols. Other organic solvents include but are not limited to perfluorocarbons, acetone, dichloromethane, chloroform, ethyl acetate, methyl tert-butyl ether, acetonitrile, dimethyl formamide and others. A preferred solvent for spray-drying or solvent evaporation is an organic solvent or a mixture of at least two organic solvents, especially a mixture of two solvents. More preferably the solvent for spray-drying is dichloromethane, chloroform, methanol or a mixture thereof, especially a mixture of dichloromethane and methanol, preferably in a weight ratio of 80/20 or 90/10. In a solvent for spray-drying or solvent evaporation that is a mixture of two organic solvents each of the organic solvent can be present in an amount ranging from 1 to about 99% by weight meaning that if the first organic solvent is present in a certain amount the second organic solvent is present in the amount that is missing to 100% (w/w).

The present invention also provides a pharmaceutical preparation comprising the composite according to the invention. Accordingly, the present invention is also directed to a pharmaceutical preparation comprising the composite.

Preferably, the pharmaceutical preparation is for oral administration. Therefore, the present invention is also directed to a pharmaceutical preparation, which is a pharmaceutical preparation for oral administration.

More preferably still, the pharmaceutical preparation is an immediate release preparation. Therefore, the present invention is further directed to pharmaceutical preparation, which is an immediate release preparation.

In exemplary embodiments, the pharmaceutical preparation, preferably a tablet, is characterized by a disintegration time of 30 minutes or less, such as 20 minutes or less, preferably 15 minutes or less, and more preferably 10 minutes or less. The disintegration time referred to above is measured in 0.01N HCl at 37° C. in a disintegration apparatus according to USP-NF <701> (USP39-NF34 Page 537; Pharmacopeial Forum: Volume No. 34(1) Page 155) Disintegration: The apparatus consists of a basket-rack assembly, a 1000-mL, low-form beaker for the immersion fluid, a thermostatic arrangement for heating, and a device for raising and lowering the basket in the immersion fluid. The basket-rack assembly moves vertically along its axis and consists of six open-ended transparent tubes; the tubes are held in a vertical position by two plates. Attached to the under surface of the lower plate is a woven stainless steel wire cloth. If specified in the individual monograph, each tube is provided with a cylindrical disk. The disk is made of a suitable transparent plastic material. Place 1 dosage unit in each of the six tubes of the basket and add a disk. Operate the apparatus, using the specified medium as the immersion fluid, maintained at 37±2°. At the end of the time limit or at preset intervals, lift the basket from the fluid, and observe whether the tablets have disintegrated completely.

In a preferred embodiment, the pharmaceutical preparation according to the present invention is a capsule comprising the composite and optionally one or more pharmaceutically acceptable excipients. The capsule itself may be any pharmaceutically acceptable capsule, such as a hard gelatin capsule, but should preferably be easily dissolvable.

In an exemplary embodiment, the pharmaceutical preparation is a capsule, which contains a filler consisting of 40 to 100% (w/w), for instance at least 50% (w/w), more preferably at least 70, 80, 90, 95 or 99% (w/w) of the composite according to the present invention; and 0 to 60% (w/w), i.e. the remainder (difference to 100% (w/w)) of the filler, of at least one pharmaceutically acceptable excipient, preferably selected from a filler, a lubricant, a glidant, and an inorganic alkaline metal salt, based upon the total weight of the filler. In other words, the capsule does not count in the calculation of the weight percentages as given herein.

A preferred embodiment of the invention is directed to pharmaceutical preparation, which is a capsule, which contains 40 to 100% (w/w) of the composite; and 0 to 60% (w/w) of at least one pharmaceutically acceptable excipient, preferably selected from a filler, a disintegrant and a lubricant, based upon the total weight of all material contained in the capsule.

The term "filler" as used herein is an agent increasing the bulk of the pharmaceutical preparation by providing the quantity of material which is needed to form such pharmaceutical preparation. A filler also serves to create desired flow properties and compression characteristics in the preparation of tablets and capsule fillers. Fillers usable in the present invention may be a sugar alcohol such as sorbitol or mannitol, dulcitol, xylitol or ribitol, preferably sorbitol or mannitol, particular preferably mannitol, a sugar such as glucose, fructose, mannose, lactose, saccharose or maltose, preferably lactose, saccharose or maltose, particular preferably lactose, a starch such as potato starch, rice starch, maize starch or pregelatinized starch, preferably maize starch or pregelatinized starch, particular preferably maize starch, a cellulose such as powdered cellulose or microcrystalline cellulose, preferably microcrystalline cellulose, or a mixture thereof. In a particularly preferred embodiment of the invention the pharmaceutical preparation comprises lactose and/or microcrystalline cellulose as filler.

The term "disintegrant" as used herein refers to a compound that expands and dissolves when wet, to cause disintegration of tablets or granulates to break apart and release the active pharmaceutical agent. The disintegrant also functions to ensure that the compounds are in contact with the solvent, such as water. Disintegrants serve to disintegrate tablets or granules etc. and thus enhance dissolution of the solid dosage form upon contact with the liquid dissolution medium. Suitable disintegrants include crospovidone (cross linked polyvinyl N-pyrrolidone), carboxymethylcellulose and salts and derivatives thereof, such as crosslinked derivatives, for instance croscarmellose sodium (cross-linked polymer of carboxymethylcellulose sodium) sodium carboxymethyl glycolate, sodium starch glycolate, carrageenan, agar, and pectin. Crospovidone and croscarmellose sodium are particularly preferred. Disintegrants are present in the pharmaceutical preparation according to the invention in a proportion of 0 to 20% (w/w), preferably 4 to 15% (w/w), particularly preferably 5 to 10% (w/w), most preferably about 6% (w/w).

The term "lubricant" as used herein refers to an inactive ingredient used to prevent sticking of ingredients to one another in capsule filling or tablet compressing machines. A lubricant reduces the sliding friction of the tableting material and ram in the mould during the tableting operation and to prevent sticking to the rams. Suitable lubricants are alkaline-earth metal salts of fatty acids, such as magnesium stearate or calcium stearate, fatty acids, such as stearic acid, higher fatty alcohols such al cetyl alcohol or stearyl alhohol, fats such as glyceryl dipalmitostearate, glyceryl distearate, stearin or glyceryl dibehenate, alkaline-earth metal salts of C16-C18 alkyl substituted dicarbonic acids such as sodium stearyl fumarate, hydrated vegetable oils such as hydrated castor oil or hydrated cotton seed oil, or minerals such as talc. Preferred lubricants are magnesium stearate, stearic acid or sodium stearyl fumarate as lubricant, particular preferred is magnesium stearate. Lubricants are present in the pharmaceutical preparation according to the invention in a proportion of 0 to 5% (w/w), preferably 0 to 3% (w/w), particularly preferably 0.25 to 2% (w/w), most preferably about 0.5% (w/w).

The term "glidant" as used herein refers to an inactive ingredient used as a flow aid that improves the flow characteristics of particulates such as powders or granules. In the present invention flow characteristics of the composite or the mixtures containing the composite during further processing such as encapsulation or tableting. Nonlimiting examples of glidants for use in the present invention include colloidal silicon dioxide (Aerosil 200, Cab-O-Sil), talc, magnesium carbonate, and combinations thereof. Glidants are present in the pharmaceutical preparation according to the invention in a proportion of 0 to 7.5% (w/w), preferably 0 to 2% (w/w), particularly preferably 0.5 to 2% (w/w), most preferably about 1% (w/w).

Inorganic alkaline metal salts, i.e. salts made up of ions of alkaline metals and inorganic acid anions, have relatively recently been found useful for enhancing dissolution and include sodium chloride, sodium sulphate, sodium carbonate, sodium bicarbonate, sodium phosphate, sodium dihydrogen phosphate, potassium chloride, potassium carbonate, and potassium bicarbonate. Sodium chloride is particularly preferred.

As will be shown by way of examples, capsule formulations may comprise, for instance, 100, 99.5, 99, 90, 80, 75, 70, 60 or 50% (w/w) of the composite respectively solid dispersion, or any range enclosed by any combination of those values. The remainder of the filler (difference to 100% (w/w)) is made up by at least one pharmaceutically acceptable excipient, as set out above.

In an exemplary embodiment, the pharmaceutical is a capsule containing a filler comprising:
50 to 100% (w/w) of the composite according to the invention;
0 to 20% (w/w) of disintegrant;
0 to 50% (w/w) of a filler;
0 to 5% (w/w) of a lubricant;
0 to 5% (w/w) of a glidant
0 to 20% (w/w) of an inorganic alkaline metal salt; and a total of 0 to 20% (w/w) of one or more additional pharmaceutically acceptable excipients, based upon the total weight of the tablet.

Filler may be present in the above exemplary embodiment, for instance, in a range of 5 to 50% (w/w), or a range of 7.5 to 50% (w/w), or a range of 10 to 40% (w/w), for instance.

Inorganic alkaline metal salt is preferably present in the above exemplary embodiment, and may be comprised in an amount of 2.5 to 20% (w/w), or 5 to 17.5% (w/w), for instance, or at least 7.5% (w/w), for instance around 10 or 15% (w/w).

In a more preferred embodiment, the pharmaceutical preparation is selected from a tablet and a granulate, and therefore typically comprises at least one pharmaceutically acceptable excipient. The at least one pharmaceutically acceptable excipient is preferably selected from a filler, a disintegrant, a lubricant, an inorganic alkaline metal salt or a combination thereof. Accordingly, the present invention is also directed to a pharmaceutical preparation, which is a tablet comprising optionally one or more pharmaceutically acceptable excipient selected from a filler, a disintegrant, a glidant and a lubricant.

In an exemplary embodiment, the pharmaceutical is a tablet comprising:
i) 25 to 100% (w/w) of the composite;
ii) 0 to 45% (w/w) of a filler;
iii) 0 to 20% (w/w) of disintegrant;
iv) 0 to 5% (w/w) of a lubricant;
v) 0 to 7.5% (w/w) of glidant; and
vi) a total of 0 to 20% (w/w) of one or more additional pharmaceutically acceptable excipients, based upon the total weight of the tablet.

The one or more additional pharmaceutically acceptable excipients may include one or more selected from preservatives, antioxidants, sweeteners, flavours, dyes, surfactants, and wicking agents.

Many excipients may exert more than one function, depending on the other components of the pharmaceutical dosage form. For the sake of clarity, in particular in calculating weight percentages, each pharmaceutically acceptable excipient used in a pharmaceutical preparation according to the present invention is preferably associated with one functionality only, i.e. is either regarded as a disintegrant or a lubricant.

In another exemplary embodiment, the pharmaceutical preparation is a tablet comprising:
- i) 60 to 80% (w/w) of the composite;
- ii) 10 to 30% (w/w) of a filler;
- iii) 4 to 15% (w/w) of disintegrant;
- iv) 0 to 3% (w/w) of a lubricant;
- v) 0 to 5% (w/w) of a glidant; and
- vi) a total of 0 to 10% (w/w) of one or more additional pharmaceutically acceptable excipients,
- based upon the total weight of the tablet.

In a further exemplary embodiment, the pharmaceutical preparation is a tablet comprising:
- i) 65 to 75% (w/w) of the composite according to any of claims 1 to 8;
- ii) 15 to 25% (w/w) of a filler;
- iii) 5 to 10% (w/w) of disintegrant;
- iv) 0.25 to 2% (w/w) of a lubricant;
- v) 0.5 to 2% (w/w) of a glidant; and
- vi) a total of 0 to 10% (w/w) of one or more additional pharmaceutically acceptable excipients,
- based upon the total weight of the tablet.

Preferably, in those embodiments, the filler is lactose and/or microcrystalline cellulose, the disintegrant is selected from crospovidone, carboxymethylcellulose and salts and derivatives thereof, especially croscarmellose sodium, the lubricant is selected from magnesium stearate, calcium stearate and sodium stearyl fumarate and/or the glidant is selected from colloidal silicon dioxide and derivatives thereof. In an especially preferred embodiment the filler is lactose and microcrystalline cellulose, the disintegrant is croscarmellose sodium, the lubricant is magnesium stearate and the glidant is colloidal silicon dioxide.

Preferably, the total of one or more additional pharmaceutically acceptable excipients is 0 to 10% (w/w), 0 to 7.5% (w/w), 0 to 5% (w/w), 0 to 2.5% (w/w) or 0 to 1% (w/w), for instance 0% (w/w).

Of course, the tablet may be coated, to improve taste and/or appearance and/or to protect the tablet from external influences such as moisture. Any coating shall not count towards the total of 100% (w/w) of pharmaceutically active ingredients and drug substance making up the tablets, as listed above. For film-coating, macromolecular substances, such as modified celluloses, including hydroxypropyl methylcellulose (HPMC), polyvinyl alcohol (PVA), polymethacrylates, polyethylene glycols, and zein may be used, for example. The thickness of the coating is preferably less than 100 µm.

The present invention also provides a method for preparing the composite, which comprises spray-drying, co-precipitation or lyophilisation, preferably co-precipitation spray-drying, most preferably spray-drying. Accordingly, the present invention is also directed to a method for preparing the composite, the method comprising spray-drying, co-precipitation or lyophilisation, preferably co-precipitation and spray-drying, more preferably spray-drying.

In an exemplary embodiment, the method comprises:
- (a) dissolving 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile and the polymer of the polymeric matrix to be formed, and optionally one or more pharmaceutically acceptable excipient in a solvent,
- (b) spray-drying of the solution prepared by step (a) to form the composite
- (c) and optionally drying the composite, preferably under reduced pressure.

Of course, dissolving may comprise dissolving the API and polymer in the solvent, which may be done successively by firstly dissolving the API to form a solution of the API and secondly adding and dissolving the polymer to the solution of API or vice versa, i.e. by firstly dissolving the polymer in the solvent and then adding the polymer. Alternatively, solutions of the API and the polymer can be prepared separately and then both solutions are unified to one solution.

Suitable spray-drying techniques which can be used for preparation of the particles are well known and described, for example, by K. Masters in "Spray-drying Handbook", John Wiley & Sons, New York, 1984. In a preferred embodiment, atomization of the liquid is performed by using a nozzle. Examples of suitable spray-driers include lab scale spray-dryers from Buchi, such as the Mini Spray Dryer 290, or a MOBILE MINOR™, or a Pharma Spray Dryer PharmaSD® from GEA Niro.

The spray-drying conditions have a major impact on product properties, solvent content, particle size, morphology and the extent of degradation API and polymer. Temperature is the most important process parameter, since the exposure of Compound and polymer to high temperature could cause degradation. For the spray-dryer, two temperatures have to be controlled: inlet temperature and outlet temperature. The former is an independent process parameter and it can be set by the operator, the latter is dependent e.g. on the liquid feed rate, the atomizing gas volumetric flow rate (if used), the drying gas volumetric flow rate, and the inlet temperature chosen. The process parameters can be readily accomplished by routine experimentation based upon the common general knowledge of the person skilled in the art.

According to an appropriate embodiment of the invention the parameters of the spray-drying process are chosen in a way that an outlet temperature is achieved that falls in the range of about 25° C. to about 50° C., preferably in the range of about 25° C. and 40° C., and, more preferably, that the outlet temperature is at about 30° C.

Suitable drying techniques which can be used for the optional drying step include ordinary techniques known in the art, such as, for example drum, belt and tray drying. Such techniques can be performed under air or nitrogen atmosphere at normal or reduced pressure, e.g. under vacuum. Drying under reduced pressure is preferred.

The composite prepared can be used for the preparation of pharmaceutical preparations such as tablets or capsules. An exemplary method for preparing a pharmaceutical preparation, which is a tablet, comprising a composite, comprises
- (a) conducting the method as described above to form the composite;
- (b) optionally granulating the mixture of the composite and the one or more pharmaceutically acceptable excipients, preferably by roller compaction;
- (c) mixing the composite and one or more pharmaceutically acceptable excipients;
- (d) tableting the mixture prepared by step (b) or the granulate prepared by step (c); and
- (e) optionally film coating of the tablets prepared by step (d).

It is to be understood that mixing the composite and excipients and granulating the mixture may be part of the same step, i.e. occur simultaneously.

The term "roller compaction" refers to a process in which fine powders are forced between two counter rotating rolls and pressed into a solid compact or ribbon. Roller compacting can be carried out with any suitable roller compactor known to the skilled person. Suitable roller compactors include, for example, a Fitzpatrick® Chilsonator IR220 roller compactor of the Fitzpatrick Company, USA. The process parameters, especially the roll force, can be readily accomplished by routine experimentation based upon the common general knowledge of the person skilled in the art. Suitable roll force may be, for example, in the range from 2 to 16 kN/cm, more preferably in the range from 4 to 12 kN/cm and most preferably in the range from 4 to 8 kN/cm.

Tableting respectively compressing into tablets can be performed with commonly used eccentric presses or rotary presses.

An exemplary method for preparing a pharmaceutical preparation, which is a capsule, comprising a composite, comprises (a) conducting the method to form the composite;

(b) optionally mixing the composite and one or more pharmaceutically acceptable excipient and optionally granulating the mixture obtained, preferably by roller compaction;

(c) filling the mixture or granulate prepared by step (b) or the composite prepared by step (a) into capsules.

As set out above in the introductory section, 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile has been found to exhibit valuable properties as a ATM kinase inhibitor that finds application in the treatment of cancer. It is currently being investigated in clinical trials.

Accordingly, the present invention provides the composite respectively pharmaceutical preparation as described above, for use in the treatment of cancer.

Optionally the treatment of cancer further comprises radiotherapy. Accordingly, the present invention is also directed to the pharmaceutical preparation of the present invention for use in the treatment of cancer optionally together with radiotherapy. Suitable radiotherapy treatments are described in WO 2012/028233 A1 and incorporated by reference herein.

Optionally, in the alternative or in addition to radiotherapy, the treatment of cancer may comprise chemotherapy. Accordingly, the present invention is also directed to the pharmaceutical preparation for use in the treatment of cancer according to claim 23, wherein the treatment further comprises chemotherapy.

Suitable pharmaceutically active ingredients that may be used in chemotherapy in combination with 3-Fluoro-4-[7-methoxy-3-methyl-8-(1-methyl-1H-pyrazol-4-yl)-2-oxo-2, 3-dihydro-imidazo[4,5-c]quinolin-1-yl]-benzonitrile include cisplatinum and etoposide or a combination thereof, to name but one example.

Accordingly, the present invention also provides a method of treating cancer in a patient in need thereof, comprising administering to the patient a pharmaceutical preparation in accordance with the present invention, optionally in combination with radiotherapy or chemotherapy or both. In an exemplary embodiment, the present invention provides a method of treating a cancer selected from colon, lung, head and neck, pancreatic, and histological subtypes thereof, in a patient in need thereof, comprising administering to said patient 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile, or a pharmaceutically acceptable salt thereof in a composite or pharmaceutical preparation according to the present invention, in combination with at least one additional therapeutic agent selected from etoposide and a platin.

In the following, the present invention will be described by reference to exemplary embodiments thereof, which shall not be regarded as limiting the invention.

DETAILED DESCRIPTION OF THE INVENTION

Example 1

Solid dispersions comprising either 10 or 20% (w/w) Compound and either 90 or 80% (w/w) polymeric matrix are prepared by spray drying using a custom-built lab-scale spray dryer. The polymers used are: cellulose acetate phthalate (CAP), Eudragit® L100, HPMCAS-L and HPMCAS-M. 10 or 20 g solids are dissolved in a mixture of methylene chloride/methanol 80/20 (w/w) to a solid content of 2.5 or 5.0% (w/w) and spray dried using the following conditions:

Atomization: pressurized nozzle with 150 psi atomizing pressure; Drying gas flow rate: 500 g/min; Liquid feed rate: 40 g/min; Inlet temperature: 105° C.; Outlet temperature: 40° C.; Secondary drying: vacuum desiccation for 2-4 days.

Dissolution tests are run for all of the above samples, using the following test conditions: Spray dried powders are dispersed to 200 µg Compound per mL in 0.01 M HCl at 37° C. (time point −30 min). 30 minutes after dispersion, a concentrated solution of simulated intestinal fluid (SIF; for details see Galia et al., Evaluation of Various Dissolution Media for Predicting In Vivo Performance of Class I and II Drugs. Pharm. Research, Vol. 15 No. 5. 1998)) powder in phosphate buffered saline (PBS) is added to the samples to a resulting concentration and pH of 100 µg Compound per mL in 0.5% (w/w) SIF powder in PBS pH 6.5 (time point 0 min).

At the according time points, samples are centrifuged and an aliquot of the supernatant analysed using HPLC. The remainder of the samples are redispersed. Sampling time points: −25, −15, −5 minutes. Buffer change at 0 minutes. Further sampling at 4, 10, 20, 40, 90 and 1200 minutes.

Figure 1:
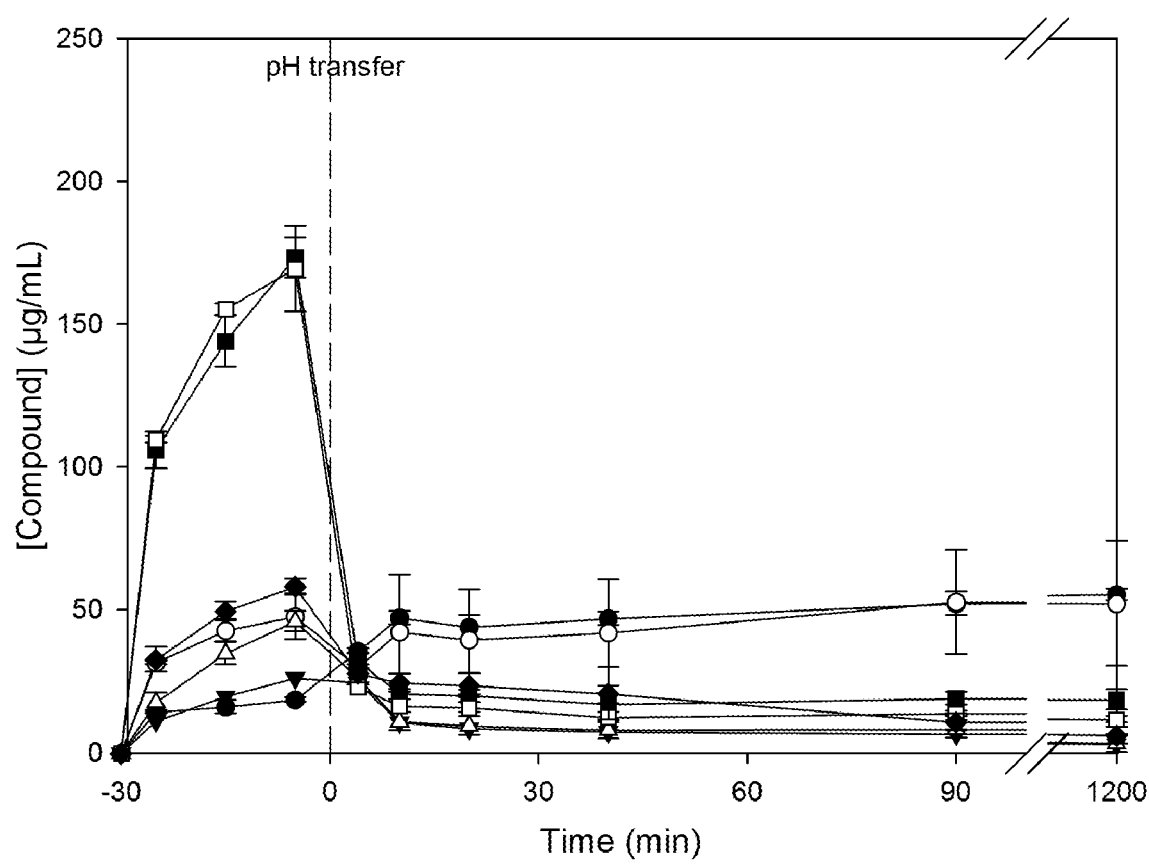
FIG. 1 shows dissolution curves for various embodiments of solid dispersions as described in EXAMPLE 1. Solid spheres: 10% Compound in cellulose acetate phthalate (CAP); open spheres: 20% Compound in CAP; solid triangles: 10% Compound in Eudragit® L100; open triangles: 20% Compound in Eudragit® L100; solid squares: 20% Compound in HPMCAS-M; open squares: 20% Compound in HPMCAS-L; solid diamonds: crystalline Compound.

The resulting dissolution curves are illustrated in FIG. 1. The solid dispersions in HPMCAS show the highest supersaturation in the gastric medium, but precipitate quickly upon transition to intestinal buffer. No difference is observed between the different grades of HPMCAS. Solid dispersions in Eudragit® L do not show supersaturation, independent of drug load. Solid dispersions in CAP show less free drug in the gastric medium than crystalline Compound, but considerable supersaturation upon transition to intestinal medium. The supersaturation is independent of drug load and remained stable after 20 hours.

X-ray diffractometric analysis of the solid dispersions in CAP shows no evidence of crystalline material.

Example 2

Further experiments are carried out on the preferred CAP based solid dispersions using the same equipment as in Example 1. Solid dispersions comprising either 15, 18, 20, 25 or 30% (w/w) Compound and either 85, 82, 80, 75, 70% (w/w) CAP are prepared by spray drying. The solids are dissolved in a mixture of methylene chloride/methanol 90/10 (w/w) and spray dried using the conditions described in Example 1.

The resulting dispersions have glass transition temperatures between 146-149° C. at <5% relative humidity, and between 80-84° C. at 75% relative humidity. X-ray diffractometric analysis of the solid dispersions in CAP show no evidence of crystalline material independent of the drug load. The achieved supersaturation is comparable for all drug loads and similar to the CAP solid dispersion prototypes shown in Example 1.

Example 3

Further process optimization is performed using a pilot scale commercial spray dryer (GEA Niro PSD-1). Two individual batches of solid dispersions comprising 20% (w/w) Compound and 80% (w/w) CAP are prepared by spray drying. 3000 g of solids are dissolved in a mixture of methylene chloride/methanol 90/10 (w/w) to a solid content of 3.9% (w/w) and spray dried using the following conditions:

Atomization: pressurized nozzle with 450 psi atomizing pressure; Drying gas flow rate: 1850 g/min; Liquid feed rate: 210 g/min; Inlet temperature: 95° C.; Outlet temperature: 35° C.; Secondary drying: tray drying at 40° C./15% relative humidity for 18 hours, or tray drying at 40° C./15% relative humidity for 13 hours followed by 2 hours at 40° C./30% relative humidity.

The spray drying yield (before secondary drying) is between 99-101%. The batch dried only at 15% relative humidity has a residual content of methylene chloride of 100 ppm, and <100 ppm of methanol (limit of quantification (LOQ)). The batch dried at 15 and 30% relative humidity has both methylene chloride and methanol <100 ppm (LOQ). Both batches show comparable supersaturation as observed in Examples 1 and 2. The glass transition temperature is 145° C. at <5% relative humidity for both batches. X-ray diffractometric analysis of the solid dispersions in CAP shows no evidence of crystalline material. The water content is determined between 2.5 and 2.8% by Karl Fischer titration. The volume-weighted particle size distribution is determined by laser diffraction as 7/23/49 µm ($d_{10}/d_{50}/d_{90}$).

Example 4

Solid dispersions comprising 20% (w/w) Compound and 80% (w/w) polymeric matrix are prepared by spray drying using a custom-built lab-scale spray dryer. The polymers used are: CAP, HPMCAS-H, HPMCAS-M and HPMCP HP50. Between 8-13 g solids are dissolved in a mixture of methylene chloride/methanol 90/10 (w/w) to a solid content of 3% (w/w) and spray dried using the following conditions:

Atomization: pressurized nozzle with 140 psi atomizing pressure; Drying gas flow rate: 450 g/min; Liquid feed rate: 35 g/min; Inlet temperature: between 81-91° C.; Outlet temperature: 35° C.; Secondary drying: convection tray dryer at 40° C. for 15 hours.

The spray drying yield is between 93-98%. The resulting dispersions have glass transition temperatures between 113-114° C. at <5% relative humidity, and between 58-62° C. at 75% relative humidity.

Figure 2:
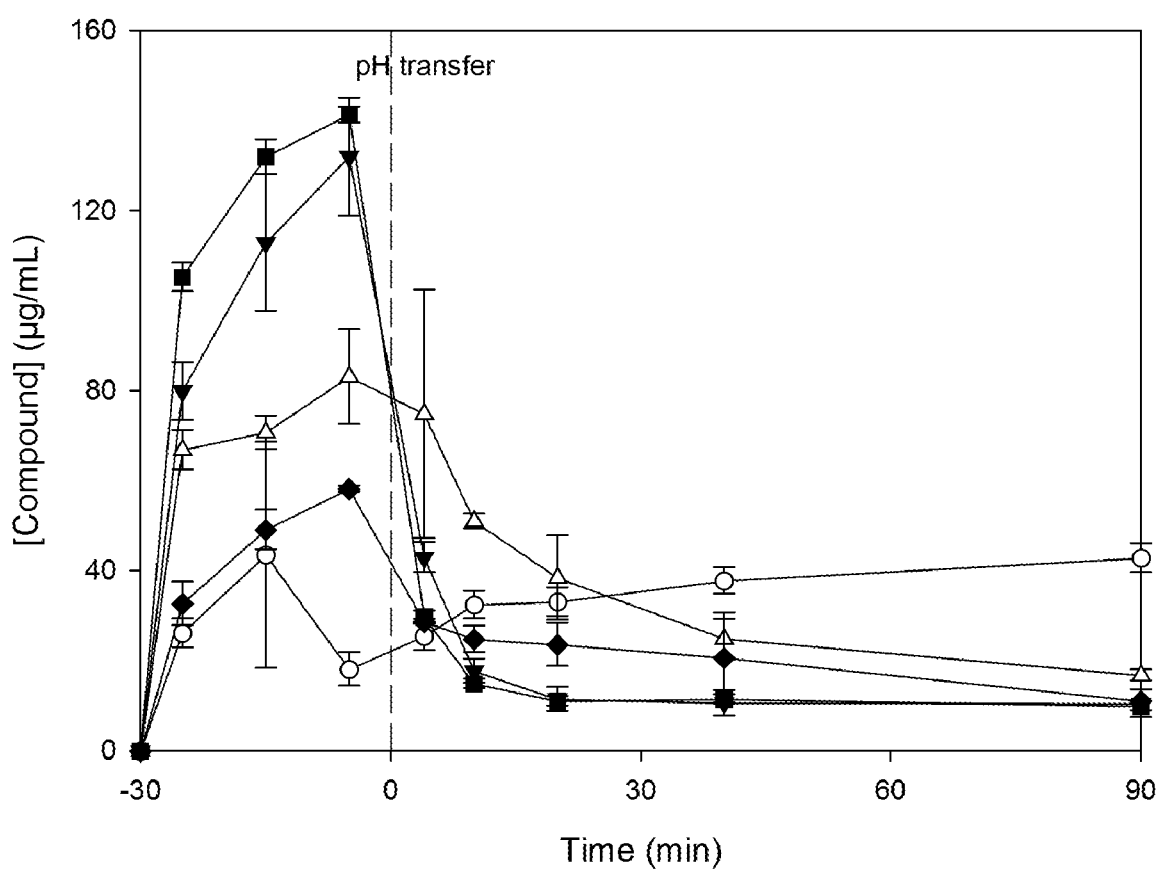
FIG. 2 shows dissolution curves for various embodiments of solid dispersions as described in EXAMPLE 4. Open Spheres: 20% Compound in CAP; solid triangles: 20% Compound in HPMCAS-M; open triangles: 20% Compound in HPMCAS-H; solid squares: 20% Compound in HPMCP HP50; solid diamonds: crystalline Compound.
Figure 3:
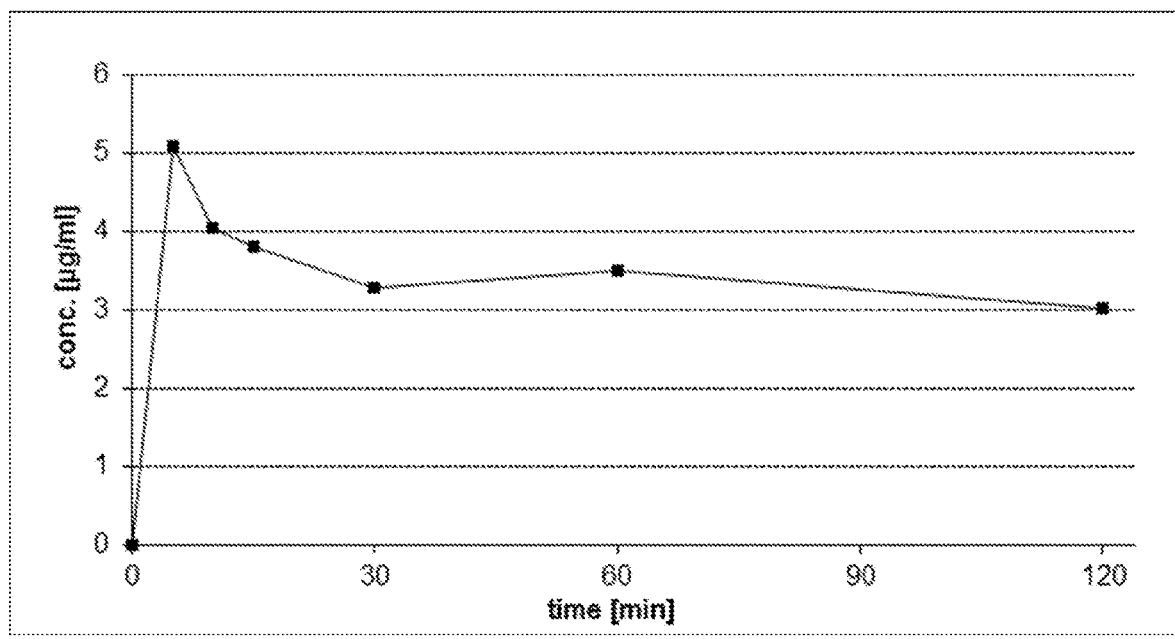
FIG. 3 shows a dissolution curve of a coprecipitate containing 16% (w/w) of Compound in CAP in FaSSIF at pH 6.5 as described in Example 5.

Dissolution experiments are carried out according to Example 1. The resulting dissolution curves are illustrated in FIG. 2. The solid dispersion in HPMCP shows the highest supersaturation in the gastric medium, followed by rapid precipitation upon transition to the intestinal buffer. The solid dispersions in HPMCAS-M show a higher supersaturation in the gastric medium than a similar formulation from Example 1, but precipitate equally upon transition to the intestinal buffer. The solid dispersions in HPMCAS-H surprisingly show a lower supersaturation in the gastric medium than M and L grades, and sustain the supersaturation until 45 minutes after transition to the intestinal buffer.

Example 5 Co-Precipitation with CAP

A solid dispersion comprising 16% (w/w) Compound and 84% (w/w) polymeric matrix (CAP) is prepared by co-precipitation. A clear solution of 16 mg/ml Compound and 64 mg/ml polymer (resembling 20% (w/w) of compound to polymer) in DMSO is prepared at 70° C. under stirring. The solution is subsequently cooled to ambient temperatures and remains clear. 1.3 ml of the clear DMSO solution is poured into the vortex of 15 ml of citric acid pH 4.0 under vigorously stirring in a beaker. The resulting suspension is filtered and the obtained cake washed with 20 ml hydrochloric acid solution pH 2.0. The washed cake is pre-dried by vacuum filtration and subsequently dried at 50° C. under nitrogen purge. The difference between the theoretical concentration of 20% (w/w) Compound to the final concentration of 16% (w/w) in the matrix results from loss of Compound during the precipitation as well as the washing steps.

Dissolution test conditions: coprecipitate is dispersed to 6.7 mg/mi in a FaSSIF-V1 solution pH 6.5. FaSSIF powder is obtained from biorelevant (Na-taurocholate 3.0 mM, Lecithin 0.75 mM, NaCl 105.9 mM, $NaH_2PO_4$ 28.4 mM, NaOH 8.7 mM, pH 6.5) at 37° C. At the according time points, aliquots of the suspension are filtered and the filtrate analysed using HPLC. Sampling time points are: 5, 10, 15, 20, 30, 45, 60, 90 and 120 minutes.

Figure 4:
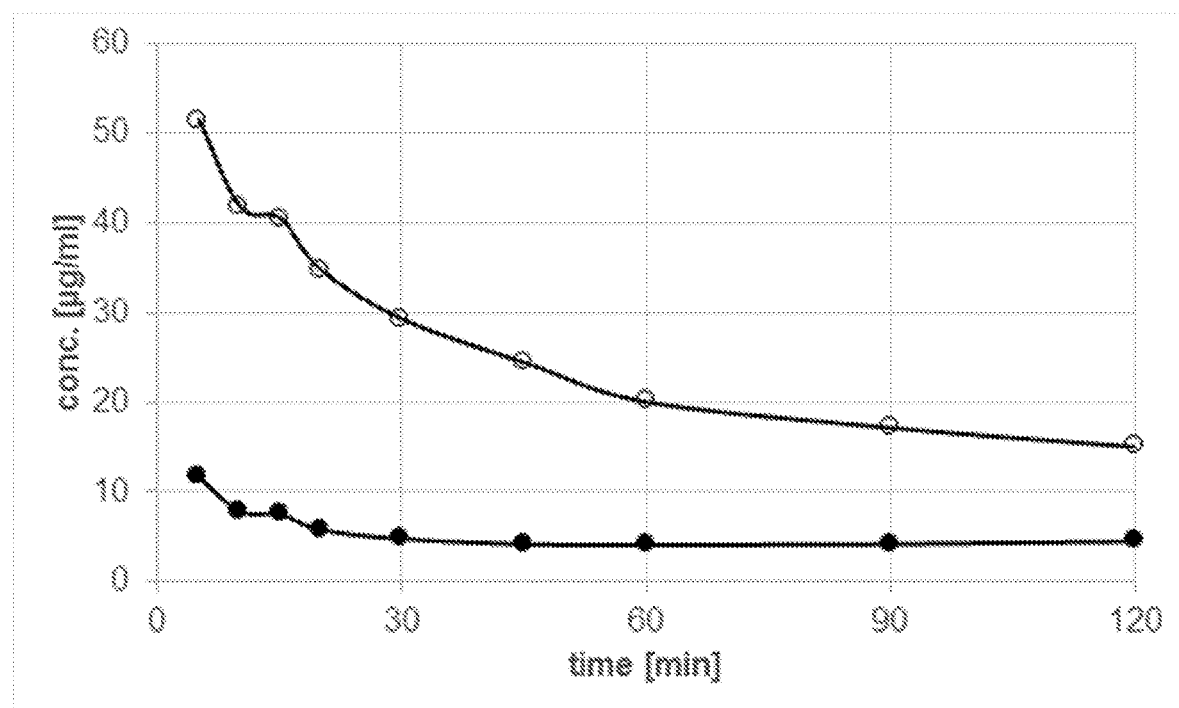
FIG. 4. Shows dissolution curves of hot melt extrudates containing 10% Compound in PVAc-PVCap-PEG (open symbols) or HPMCAS-L (closed symbols) as described in Example 6.

The resulting dissolution curve is illustrated in FIG. 4. Compared to the solubility of the Compound in FaSSIF of approx. 0.25 µg/ml the coprecipitate shows a good supersaturation of 5 µg/ml with a slight recrystallization down to approx. 3 µg/ml.

Example 6 Hot Melt Extrusion with
PVAc-PVCap-PEG and HPMCAS-L

Solid dispersions comprising 10% (w/w) Compound and 90% (w/w) polymeric matrix are prepared by hot melt extrusion. The polymers used are: HPMCAS-L and PVAc-PVCap-PEG. Approx. 10 g of a physical mixture containing 10% (w/w) Compound and 90% (w/w) polymeric matrix is blended with a Turbula T2F for 10 min. The obtained blend is subsequently extruded using a Haake Minilab with conical, co-rotating twinscrews at 100 rpm. For PVAc-PVCap-PEG an extrusion temperature of 170° C. and for HPMCAS-L of 180° C. is used. For milling of the strands a Pulverisette 23 with two 10 mm zirconium oxide grinding balls is used at an oscillation of 50 Hz.

Dissolution tests are run for all of the above samples, using the following test conditions: milled strands are dispersed to 200 µg Compound per mL in 1.3 ml FaSSIF-V1 pH 6.5 from biorelevant (Na-taurocholate 3.0 mM, Lecitihin 0.75 mM, NaCl 105.9 mM, $NaH_2PO_4$ 28.4 mM, NaOH 8.7 mM, pH 6.5) at 37° C. At the according time points, samples are centrifuged and an aliquot of the supernatant analysed using HPLC. The remainder of the samples are redispersed. Sampling time points are: 5, 10, 15, 20, 30, 45, 60, 90 and 120 minutes.

The resulting dissolution curves are illustrated in FIG. 4. Both solid dispersions show a strong supersaturation, which is even more pronounced for PVAc-PVCap-PEG (approx. 50 µg/ml at 5 min.) compared to HPMCAS-L (approx. 15 µg/ml at 5 min.). PVAc-PVCap-PEG shows a rather strong recrystallization, but the residual solubility in FaSSIF after 120 min with approx. 15 µg/ml is rather high. HPMCAS-L stabilizes supersaturation better than PVAc-PVCap-PEG and ends at approx. 4 µg/ml after 120 min.

The strong supersaturation is rather surprising as powder X-ray diffraction and polarized light microscopy analysis demonstrate that under the used conditions no purely amorphous solid dispersions are obtained.

Example 7: Exemplary Tablet Formulations (w/o Coating)

Tablets are produced with a composition comprising the following ingredients at the indicated weight percentage of the tablet weight. The blends are pre-compacted to a solid fraction of 0.5, milled and sieved through a 800 µm screen. The resulting granules are compressed to achieve tablets with a tensile strength from 1.5 to 3.5 MPa.

| Tablet # | Composition | % (w/w) | Disintegration time [s] |
|---|---|---|---|
| 1 | Solid dispersion in 80 wt % CAP | 50.0 | 15 |
|   | Microcrystalline cellulose (Avicel® PH101) | 28.3 | |
|   | Lactose Monohydrate 310 | 14.2 | |
|   | Croscarmellose sodium | 6.0 | |
|   | Colloidal silicon dioxide | 1.0 | |
|   | Magnesium stearate | 0.5 | |
| 2 | Solid dispersion in 80 wt % CAP | 50.0 | 14 |
|   | Microcrystalline cellulose (Avicel® PH101) | 28.3 | |
|   | Lactose Monohydrate 310 | 14.2 | |
|   | Crospovidone | 6.0 | |
|   | Colloidal silicon dioxide | 1.0 | |
|   | Magnesium stearate | 0.5 | |
| 3 | Solid dispersion in 80 wt % CAP | 50.0 | 15 |
|   | Microcrystalline cellulose (Avicel® PH101) | 25.7 | |
|   | Lactose Monohydrate 310 | 12.8 | |
|   | Croscarmellose sodium | 10.0 | |
|   | Colloidal silicon dioxide | 1.0 | |
|   | Magnesium stearate | 0.5 | |
| 4 | Solid dispersion in 80 wt % CAP | 62.5 | 15 |
|   | Microcrystalline cellulose (Avicel® PH101) | 20.0 | |
|   | Lactose Monohydrate 310 | 10.0 | |
|   | Croscarmellose sodium | 6.0 | |
|   | Colloidal silicon dioxide | 1.0 | |
|   | Magnesium stearate | 0.5 | |
| 5 | Solid dispersion in 80 wt % CAP | 62.5 | 15 |
|   | Microcrystalline cellulose (Avicel® PH101) | 22.0 | |
|   | Lactose Monohydrate 310 | 11.0 | |
|   | Croscarmellose sodium | 3.0 | |
|   | Colloidal silicon dioxide | 1.0 | |
|   | Magnesium stearate | 0.5 | |
| 6 | Solid dispersion in 80 wt % CAP | 62.5 | 20 |
|   | Microcrystalline cellulose (Avicel® PH101) | 20.0 | |
|   | Lactose Monohydrate 310 | 10.0 | |
|   | Sodium starch glycolate | 6.0 | |
|   | Colloidal silicon dioxide | 1.0 | |
|   | Magnesium stearate | 0.5 | |
| 7 | Solid dispersion in 80 wt % CAP | 71.4 | 12 |
|   | Microcrystalline cellulose (Avicel® PH101) | 14.1 | |
|   | Lactose Monohydrate 310 | 7.0 | |
|   | Croscarmellose sodium | 6.0 | |
|   | Colloidal silicon dioxide | 1.0 | |
|   | Magnesium stearate | 0.5 | |
| 8 | Solid dispersion in 80 wt % CAP | 62.5 | 24 |
|   | Microcrystalline cellulose (Avicel® PH101) | 22.0 | |
|   | Mannitol | 11.0 | |
|   | Croscarmellose sodium | 3.0 | |
|   | Colloidal silicon dioxide | 1.0 | |
|   | Magnesium stearate | 0.5 | |

| Tablet # | Composition | % (w/w) | Disintegration time [s] |
|---|---|---|---|
| 9 | Solid dispersion in 80 wt % CAP | 62.5 | 17 |
| | Microcrystalline cellulose (Avicel ® PH101) | 20.0 | |
| | Lactose Monohydrate 310 | 10.0 | |
| | Croscarmellose sodium | 6.0 | |
| | Colloidal silicon dioxide | 1.0 | |
| | Sodium stearyl fumarate | 0.5 | |
| 10 | Solid dispersion in 80 wt % CAP | 50.0 | 18 |
| | Microcrystalline cellulose (Avicel ® PH101) | 14.2 | |
| | Lactose Monohydrate 310 | 28.3 | |
| | Croscarmellose sodium | 6.0 | |
| | Colloidal silicon dioxide | 1.0 | |
| | Magnesium stearate | 0.5 | |
| 11 | Solid dispersion in 80 wt % CAP | 50.0 | 15 |
| | Microcrystalline cellulose (Avicel ® PH101) | 14.2 | |
| | Lactose Monohydrate 313 | 28.3 | |
| | Croscarmellose sodium | 6.0 | |
| | Colloidal silicon dioxide | 1.0 | |
| | Magnesium stearate | 0.5 | |
| 12 | Solid dispersion in 80 wt % CAP | 50.0 | 93 |
| | Microcrystalline cellulose (Avicel ® PH101) | 25.7 | |
| | Lactose Monohydrate 310 | 12.8 | |
| | Croscarmellose sodium | 6.0 | |
| | Sodium lauryl sulfate | 4.0 | |
| | Colloidal silicon dioxide | 1.0 | |
| | Magnesium stearate | 0.5 | |

In the dissolution assay as described in Example 1, all tablet formulations achieve Compound solubilities far below the Compound solubilities of the solid dispersions. However, and surprisingly, when such tablets are grounded and suspended in a suitable vehicle for oral administration and given to rats by gavage, the resulting plasma concentration of the Compound is comparable to the concentration that is obtained after administration of a similar suspension made of the solid dispersion.

Example 8: Exemplary Capsule Formulations

HPMC capsules are provided with a filler comprising the following ingredients at the indicated weight percentage of the filler. The disintegration of the formulations is below 6 minutes.

| Capsule # | Ingredient | % (w/w) |
|---|---|---|
| 1 | Solid dispersion in 80 wt % CAP | 98.75 |
| | Colloidal silicon dioxide | 1 |
| | Magnesium stearate | 0.25 |
| 2 | Solid dispersion in 80 wt % CAP | 83.75 |
| | Sodium chloride | 15 |
| | Colloidal silicon dioxide | 1 |
| | Magnesium stearate | 0.25 |

Example 9: Exemplary Capsule Formulations

HPMC capsules are provided with a filler comprising the following ingredients at the indicated weight percentage of the filler. The filler is compacted before filling to achieve a bulk density between 0.4 and 0.5 g/cm³.

| Capsule # | Ingredient | % (w/w) |
|---|---|---|
| 1 | Solid dispersion in 80 wt % CAP | 83.75 |
| | Sodium chloride | 15 |
| | Colloidal silicon dioxide | 1 |
| | Magnesium stearate | 0.25 |
| 2 | Solid dispersion in 80 wt % CAP | 68.75 |
| | Sodium chloride | 30 |
| | Colloidal silicon dioxide | 1 |
| | Magnesium stearate | 0.25 |
| 3 | Solid dispersion in 80 wt % CAP | 43.75 |
| | Sodium chloride | 45 |
| | Colloidal silicon dioxide | 1 |
| | Magnesium stearate | 0.25 |

Example 10: Exemplary Tablet Pilot Scale Compression

Tablets comprising a solid dispersion of the Compound in 80% CAP are manufactured on pilot scale equipment in strengths of 10, 50 and 100 mg Compound per tablet. About 4.2 kg blend of the solid dispersion and excipients as set forth in Example 6 Tablet #7, using half indicated the amount of silicon dioxide and magnesium stearate, are blended in a 50 L bin blender. The blend is granulated by roller compaction on pilot scale equipment using a roll force of 6 kN, 2 rpm roll speed, 2 mm gap, and a screen size of 0.8 mm. The granules are blended with the remainder of silicon dioxide and magnesium stearate and compressed on a pilot scale rotary press. Suitable press forces are chosen to compress tablets comprising 10, 50 or 100 mg Compound to a tensile strength of 2 or 3 MPa. For example, a press force of 3 kN, 10.2 kN, and 15.0 kN is used to produce round 10 mg tablets, oval 50 mg tablets, and oval 100 mg tablets to a tensile strength of 2 MPa. All tablets have acceptable appearance, disintegrate very fast (all below 1 min), have acceptable mass loss after friability (below 0.1%), and acceptable relative standard deviation of the weight of below 2% for 10 mg tablets, and below 1% for 50 and 100 mg tablets.

Example 11: Exemplary Tablet Coating

Tablets comprising 10, 50, or 100 mg of Compound are coated in a Vector LDCS pan coater. The coating solution consists of 20% (w/w) Opadry II 85F in deionized water. The solution is sprayed on a bed of about 1 kg of tablet cores in a 1.3 L pan, rotated at 22 rpm. A spray rate between 9-11 g/min and a spray time of 15-16 min while drying with a drying gas flow of 40-41 CFM, an inlet temperature of 74° C. and an outlet temperature of 43-44° C. results in a coating weight of 2.4-3.2%. The coated tablets contain 2.3-2.6% residual water, which is less than before coating. No physical or chemical degradation of the formulation is observed after coating. The coated tablets disintegrate slightly slower than the uncoated tablet cores, but disintegration is still very fast (below 1 min for 10 mg, below 2 min for 50 and 100 mg).

Tablet cores with a tensile strength of 1.7 MPa are generally deemed sufficient for coating, bulk handling, packaging etc (Pitt, K. G. and M. G. Heasley (2013). "Determination of the tensile strength of elongated tablets." Powder Technology 238: 169-175). Surprisingly, tablets compressed to 2 MPa as set forth in Example 10 show surface defects after coating. Compression to a tensile strength of 3 MPa is sufficient to avoid any defects.

The invention claimed is:

1. A composite comprising a solid dispersion of 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile, or a pharmaceutically acceptable salt thereof, in a polymeric matrix,
    wherein the polymeric matrix comprises hydroxypropyl methylcellulose acetate succinate and/or cellulose acetate phthalate.

2. The composite according to claim 1, wherein the solid dispersion is a solid solution.

3. The composite according to claim 1, wherein 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile is present in the polymeric matrix in a range of from 4 to 50 percent (w/w), based upon the total weight of the composite.

4. The composite according to claim 1, wherein the composite has a mean particle size characterized by a $d_{50}$ value in the range from 1 μm to 300 μm.

5. A granulate comprising the composite according to claim 1, wherein the granulate has a particle size characterized by a $d_{50}$ vlue of 1000 μm or less.

6. A pharmaceutical preparation comprising the composite according to claim 1.

7. The pharmaceutical preparation according to claim 6, which is a pharmaceutical preparation for oral administration.

8. The pharmaceutical preparation according to claim 6, which is an immediate release preparation.

9. The pharmaceutical preparation according to claim 6, which is a capsule comprising the composite and optionally one or more pharmaceutically acceptable excipients.

10. The pharmaceutical preparation according to claim 9, which contains 40 to 100% (w/w) of the composite; and 0 to 60% (w/w) of at least one pharmaceutically acceptable excipient, based upon the total weight of all material contained in the capsule.

11. The pharmaceutical preparation according to claim 6, which is a tablet comprising optionally one or more pharmaceutically acceptable excipient selected from a filler, a disintegrant, a glidant and a lubricant.

12. The pharmaceutical preparation according to claim 11, which comprises:
    25 to 100% (w/w) of the composite;
    0 to 45% (w/w) of a filler;
    0 to 20% (w/w) of disintegrant;
    0 to 5% (w/w) of a lubricant;
    0 to 7,5% (w/w) of glidant; and
    a total of 0 to 20% (w/w) of one or more additional pharmaceutically acceptable excipients,
    based upon the total weight of the tablet.

13. The pharmaceutical preparation according to claim 11, which comprises:
    60 to 80% (w/w) of the composite;
    10 to 30% (w/w) of a filler;
    4 to 15% (w/w) of disintegrant;
    0 to 3% (w/w) of a lubricant;
    0 to 5% (w/w) of a glidant; and
    a total of 0 to 10% (w/w) of one or more additional pharmaceutically acceptable excipients,
    based upon the total weight of the tablet.

14. The pharmaceutical preparation according to claim 11, which comprises:
    65 to 75% (w/w) of the composite;
    15 to 25% (w/w) of a filler;
    5 to 10% (w/w) of disintegrant;
    0.25 to 2% (w/w) of a lubricant;
    0.5 to 2% (w/w) of a glidant; and
    a total of 0 to 10% (w/w) of one or more additional pharmaceutically acceptable excipients,
    based upon the total weight of the tablet.

15. The pharmaceutical preparation according to claim 11, wherein the filler is selected from lactose and/or microcrystalline cellulose, the disintegrant is selected from crospovidone, carboxymethylcellulose and salts and derivatives thereof, the lubricant is selected from magnesium stearate, calcium stearate and sodium stearyl fumarate, and/or the glidant is selected from colloidal silicon dioxide and derivatives thereof.

16. A method for preparing the composite according to claim 1, the method comprising: spray-drying, co-precipitation or lyophilization.

17. A method for preparing the composite according to claim 1, the method comprising:
    (a) dissolving 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile and the polymer of the polymeric matrix to be formed, and optionally one or more pharmaceutically acceptable excipient in a solvent to form a solution,
    (b) spray-drying the solution to form the composite, and
    (c) optionally drying the composite.

18. A method for preparing a pharmaceutical preparation, which is a tablet, comprising
    (a) conducting the method according to claim 16 to form the composite;
    (b) optionally granulating a mixture of the composite and one or more pharmaceutically acceptable excipients;
    (c) mixing the composite and one or more pharmaceutically acceptable excipients;
    (d) tableting the mixture prepared by (b) or the granulate prepared by (c); and
    (e) optionally film coating of the tablets prepared by (d).

19. A method for preparing a pharmaceutical preparation, which is a capsule, comprising
    (a) conducting the method according to claim 16 to form the composite;

(b) optionally mixing the composite and one or more pharmaceutically acceptable excipient and optionally granulating the mixture obtained;

(c) filling the mixture or granulate prepared by (b) or the composite prepared by (a) into capsules.

20. A method of treating cancer comprising administering to a subject in need thereof the pharmaceutical preparation according to claim 6, optionally together with radiotherapy.

21. The method according to claim 20, wherein the treatment further comprises chemotherapy.

22. The composite according to claim 1, wherein 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile is present in the polymeric matrix in a range of from 10 to 30 percent (w/w), based upon the total weight of the composite.

23. The composite according to claim 1, wherein 3-Fluoro-4-[7-methoxy-3-methyl-8-(1-methyl-1H-pyrazol-4-yl)-2-oxo-2,3-dihydro-imidazo[4,5-c]quinolin-1-yl]-benzonitrile is present in the polymeric matrix in a range of from 15 to 25 percent (w/w) based upon the total weight of the composite.

24. The composite according to claim 1, wherein the composite has a mean particle size that is characterized by a $d_{50}$ value in the range from 20 μm to 200 μm.

25. A granulate comprising the composite according to claim 1, wherein the granulate has a particle size that is characterized by a $d_{50}$ value of 500 μm or less.

* * * * *